(12) United States Patent
Gliner et al.

(10) Patent No.: US 11,497,560 B2
(45) Date of Patent: Nov. 15, 2022

(54) WIRELESS TOOL WITH ACCELEROMETER FOR SELECTIVE POWER SAVING

(71) Applicant: Biosense Webster (Israel) Ltd., Yokneam (IL)

(72) Inventors: Vadim Gliner, Haifa (IL); Yaron Ephrath, Karkur (IL); Assaf Govari, Haifa (IL); Andres Claudio Altmann, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 437 days.

(21) Appl. No.: 15/581,230

(22) Filed: Apr. 28, 2017

(65) Prior Publication Data
US 2018/0310995 A1 Nov. 1, 2018

(51) Int. Cl.
*A61B 34/20* (2016.01)
*A61B 17/00* (2006.01)
(Continued)

(52) U.S. Cl.
CPC ............ *A61B 34/20* (2016.02); *A61B 5/0538* (2013.01); *A61B 17/00* (2013.01); *A61B 18/148* (2013.01);
(Continued)

(58) Field of Classification Search
CPC ....... A61B 34/20; A61B 17/00; A61B 5/0538; A61B 18/148; A61B 2090/064;
(Continued)

(56) References Cited

U.S. PATENT DOCUMENTS

| 5,391,199 A | 2/1995 | Ben-Haim |
| 5,443,489 A | 8/1995 | Ben-Haim |

(Continued)

FOREIGN PATENT DOCUMENTS

| EP | 2482167 A1 | 8/2012 |
| JP | 2012-120843 A | 6/2012 |

OTHER PUBLICATIONS

Extended European Search Report dated Oct. 10, 2018 for European Patent Application No. 18169708.7.
(Continued)

*Primary Examiner* — Bill Thomson
*Assistant Examiner* — Aminah Asghar
(74) *Attorney, Agent, or Firm* — Volpe Koenig (57) ABSTRACT

A method, system, and device for selective power saving may be used in medical procedures. The device may be configured to receive motion information from a detector and location information from a sensor. A processor may correlate the motion information and the location information to determine whether to maintain power to the sensor. The determination of whether to maintain power to the sensor may be based on the correlation of the motion information and the location information. The processor may determine whether the location of the device has changed and the degree of that change. The processor may also determine whether the motion information is less than a duration threshold. The duration threshold may be a user configurable threshold. The processor may power off the sensor if a duration threshold is met and/or the location of the wireless tool has not changed.

14 Claims, 4 Drawing Sheets

(51) Int. Cl.
*H04W 52/02* (2009.01)
*G06F 1/3206* (2019.01)
*A61B 90/00* (2016.01)
*A61B 18/14* (2006.01)
*A61B 5/0538* (2021.01)
*G16H 40/63* (2018.01)
*G06F 1/3296* (2019.01)
*H04W 84/18* (2009.01)

(52) U.S. Cl.
CPC .......... *G06F 1/3206* (2013.01); *G06F 1/3296* (2013.01); *G16H 40/63* (2018.01); *H04W 52/0254* (2013.01); *H04W 52/0274* (2013.01); *A61B 2017/00199* (2013.01); *A61B 2034/2048* (2016.02); *A61B 2034/2051* (2016.02); *A61B 2034/2059* (2016.02); *A61B 2090/064* (2016.02); *H04W 84/18* (2013.01)

(58) Field of Classification Search
CPC .. A61B 2017/00199; A61B 2034/2059; A61B 2034/2051; A61B 2034/2048; G06F 1/3296; G06F 1/3206; H04W 52/0274; H04W 52/0254; H04W 84/18; G16H 40/63
See application file for complete search history.

(56) References Cited

U.S. PATENT DOCUMENTS

| | | | |
|---|---|---|---|
| 5,558,091 A | 9/1996 | Acker et al. | |
| 5,825,293 A * | 10/1998 | Ahmed | A61B 5/113 340/573.1 |
| 5,944,022 A | 8/1999 | Nardella et al. | |
| 5,983,126 A | 11/1999 | Wittkampf | |
| 6,024,703 A * | 2/2000 | Zanelli | A61B 18/20 600/437 |
| 6,172,499 B1 | 1/2001 | Ashe | |
| 6,177,792 B1 | 1/2001 | Govari et al. | |
| 6,211,666 B1 * | 4/2001 | Acker | A61B 5/06 128/899 |
| 6,266,551 B1 | 7/2001 | Osadchy et al. | |
| 6,456,828 B1 | 9/2002 | Ozluturk | |
| 6,690,963 B2 | 2/2004 | Ben-Haim et al. | |
| 6,788,967 B2 | 9/2004 | Ben-Haim et al. | |
| 7,809,421 B1 * | 10/2010 | Govari | A61B 5/062 600/407 |
| 8,315,696 B2 | 11/2012 | Schwartz | |
| 9,642,529 B1 * | 5/2017 | Siddiqui | A61B 5/0008 |
| 2003/0120150 A1 * | 6/2003 | Govari | A61B 5/0031 600/424 |
| 2006/0079764 A1 * | 4/2006 | Wright | A61B 5/06 600/431 |
| 2009/0093806 A1 | 4/2009 | Govari et al. | |
| 2009/0138007 A1 | 5/2009 | Govari et al. | |
| 2010/0168576 A1 * | 7/2010 | Poland | A61B 8/4427 600/443 |
| 2010/0262012 A1 * | 10/2010 | Wu | A61B 8/00 600/459 |
| 2012/0106589 A1 * | 5/2012 | Ozawa | A61B 5/01 374/1 |
| 2013/0176869 A1 * | 7/2013 | Finlow-Bates | H04W 52/0254 370/252 |
| 2014/0013136 A1 * | 1/2014 | Dadu | G06F 1/3209 713/323 |
| 2014/0056452 A1 | 2/2014 | Moss et al. | |
| 2014/0121489 A1 * | 5/2014 | Kommu Chs | A61B 8/4427 600/407 |
| 2014/0128739 A1 * | 5/2014 | Sundaran | A61B 8/54 600/459 |
| 2014/0148808 A1 * | 5/2014 | Inkpen | G01B 7/003 606/80 |
| 2014/0305994 A1 | 10/2014 | Parihar et al. | |
| 2014/0343395 A1 * | 11/2014 | Choi | A61B 5/4851 600/409 |
| 2015/0133786 A1 * | 5/2015 | Wong | A61B 8/4427 600/441 |
| 2015/0150474 A1 * | 6/2015 | Pan | A61B 5/05 433/27 |
| 2015/0272574 A1 | 10/2015 | Leimbach et al. | |
| 2015/0272581 A1 | 10/2015 | Leimbach et al. | |
| 2015/0345985 A1 * | 12/2015 | Fung | A61B 5/02438 702/160 |
| 2016/0100772 A1 * | 4/2016 | Ikuma | A61B 5/062 600/424 |
| 2016/0135791 A1 * | 5/2016 | Park | G06F 11/1441 600/459 |
| 2016/0255422 A1 * | 9/2016 | Matsuno | A61B 5/1118 340/870.39 |
| 2017/0105703 A1 * | 4/2017 | Han | H04L 67/12 |
| 2017/0168082 A1 * | 6/2017 | Johnson | G06F 1/3234 |
| 2018/0192374 A1 * | 7/2018 | Jain | H04W 4/029 |
| 2018/0338746 A1 * | 11/2018 | Wu | A61B 8/54 |
| 2019/0069243 A1 * | 2/2019 | Bean | G06F 1/3206 |
| 2019/0117317 A1 * | 4/2019 | Abayazid | A61B 34/20 |
| 2019/0388027 A1 * | 12/2019 | Zhang | G06F 1/32 |

OTHER PUBLICATIONS

Notification of Reasons for Refusal dated Mar. 29, 2022 for Japanese Patent Application No. 2018-086377.

* cited by examiner

WIRELESS TOOL WITH ACCELEROMETER FOR SELECTIVE POWER SAVING

SUMMARY

A wireless medical tool may include a detector, a sensor, a processor, and a transmitter. The detector may be an accelerometer, and may be used to detect motion of the wireless medical tool. The sensor may be an inductor, for example a magnetic field inductor. A magnetic field inductor may also be referred to as a magnetic inductor or location sensor. The sensor may receive a signal from a field generator. For example, the signal may be a magnetic signal from a magnetic field generator.

The processor of the wireless medical tool may be configured to receive motion information from the detector and location information from the sensor. The processor may correlate the motion information and the location information and determine whether to maintain power to the sensor. The determination of whether to maintain power to the sensor may be based on the correlation of the motion information and the location information. The processor may determine whether the location of the wireless medical tool has changed and the degree of that change. The processor may also determine whether the motion information is less than a duration threshold. The duration threshold may be a user configurable threshold. The processor may power off the sensor if a duration threshold is met and/or the location of the wireless tool has not changed.

The transmitter may transmit the location information to a system console for display on a monitor. The transmission of the location information of the location information may be based on the motion information and/or the location information.

A method may be used save power in a wireless medical device. The method may determine whether movement, i.e., motion, is detected. If it is determined that the wireless medical tool has moved, power to a location sensor may be turned on. The method may then determine whether a location of the wireless medical tool has changed.

If the location of the wireless medical tool has changed, the wireless tool may transmit location information to a control console. If the location of the wireless medical tool has not changed, the method may determine whether the detected movement is less than a duration threshold. If the detected movement is greater than the duration threshold, the method may transmit the location data to the control console. If the detected movement is less than the duration threshold, the method may enter into a power saving mode. For example, a power saving mode may include shutting off power to the location sensor.

If movement is not detected, the method may start a timer. Upon expiration of the timer, the method may enter into a power saving mode. For example, the power saving mode may include shutting off power to the location sensor. If the timer has not expired, the method will continue to determine whether movement is detected.

A medical system may include a wireless medical tool, a field generator, a console, and a display. The wireless medical tool may include a detector, a sensor, a processor, and a transmitter. The detector may be an accelerometer, and may be used to detect motion of the wireless medical tool. The sensor may be an inductor, for example a magnetic field inductor. A magnetic field inductor may also be referred to as a magnetic inductor or location sensor. The sensor may receive a signal from the field generator. For example, the signal may be a magnetic signal from a magnetic field generator.

The processor of the wireless medical tool may be configured to receive motion information from the detector and location information from the sensor. The processor may correlate the motion information and the location information and determine whether to maintain power to the sensor. The determination of whether to maintain power to the sensor may be based on the correlation of the motion information and the location information. The processor may determine whether the location of the wireless medical tool has changed and the degree of that change. The processor may also determine whether the motion information is less than a duration threshold. The duration threshold may be a user configurable threshold. The processor may power off the sensor if a duration threshold is met and/or the location of the wireless tool has not changed.

The transmitter may transmit the location information to a system console for display on the display. The transmission of the location information of the location information may be based on the motion information and/or the location information.

BRIEF DESCRIPTION OF THE DRAWINGS

The present embodiments are illustrated by way of example, and not by way of limitation, in the figures of the accompanying drawings in which.

DETAILED DESCRIPTION OF THE PREFERRED EMBODIMENTS

Medical systems typically transmit signals over a fixed wire or cable to communicate with non-fixed medical tools. Traditionally, these non-fixed wired systems and tools employed a fixed wire connection to receive a constant reliable source of power. The advancement of short-range radio technology now affords medical tool manufacturers the ability to create non-fixed tools without the need for a fixed physical cable. For example, non-fixed tools meeting or complying with the Institute of Electrical and Electronics Engineers (IEEE) 802.11, IrDA (infrared data), and Ericsson Bluetooth™ specifications provide short-range radio technology to enable wireless communications.

These non-fixed wireless medical tools, however, are typically without a fixed continuous reliable power source and rely on a portable battery power source for operation when active. In addition, this portable battery power source often has a finite life of about three to four hours. Thus, if the battery is not charged or properly recharged, it could fail (i.e. run out of charge) during a procedure. Due to the critical health support requirements for these medical tools and the potential consequences of a power failure in such equipment, these tools require a highly reliable battery power management system.

These battery-operated wireless medical tools, when used under normal operation, are exposed to functional issues. One example of a functional issue is that manufacturers of medical tools seek to create tools that are as small and lightweight as possible for use in specific medical procedures, especially in ENT procedures. On the other hand, the battery-operated wireless medical tool must maintain power as long as possible, which requires the application of a larger-sized battery.

Another example of a functional issue is providing a wireless location indication at all times to the user. During a surgical or medical procedure, a physician may use numerous medical tools, but will not use all of those tools for the entirety of the procedure. Instead, a physician typically uses a battery-operated medical tool for a specific period of time and then puts it aside and uses other medical tools for other portions of the procedure, and may use the battery-operated medical tool again at a later period. Thus, battery-operated medical tools that are not in use by the physician for a period of time during the procedure are still on and constantly providing an indication of the tool's location and/or status. This poses a particular challenge for power management, since the battery of the battery-operated medical tool has a finite life and power is constantly decreasing as the medical tool is on and providing the tool's location, even during non-use. Moreover, physicians are not interested in location indication of medical tools that are set aside during a procedure; instead, physicians prefer location indication of the tool that they are currently using.

Thus, it would be advantageous to offer a system that extends the battery life of a battery-operated wireless medical tool by switching on the location sensors of the wireless tool when motion detected, and subsequently invoking a low-powered hibernation or other power saving mode when motion is not detected to ensure proper and extended medical tool operation during procedures.

A system and method for switching on a wireless tool and switching the wireless tool to a low power or hibernation mode when motion and location frequencies are detected is presented.

Figure 1:
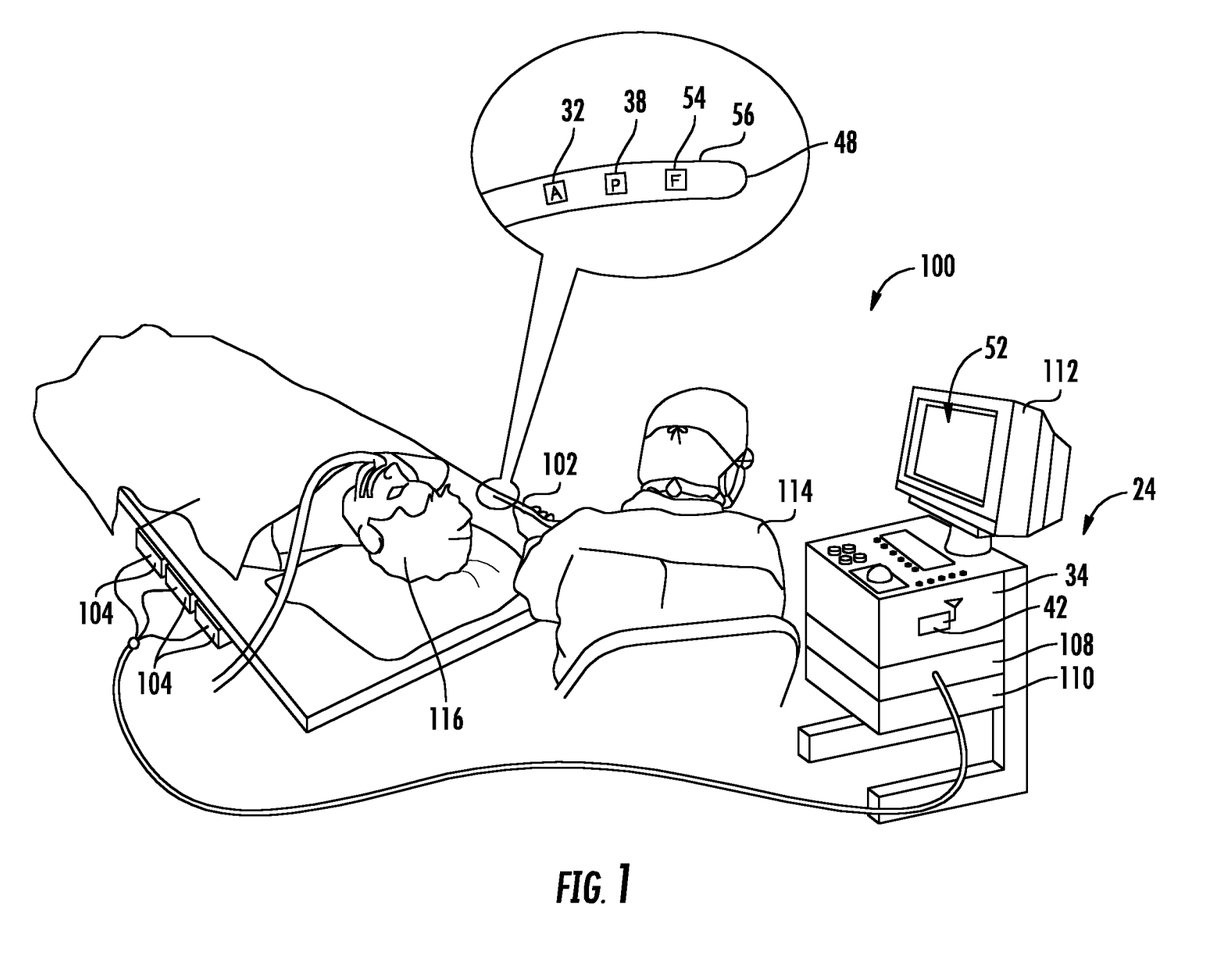
FIG. 1 is a schematic diagram of a medical system for a wireless medical tool in accordance with an embodiment of the present invention.

FIG. 1 illustrates a schematic of the medical system 100 in accordance with an embodiment of the invention. The medical system 100 includes a wireless medical tool 38, one or more field generators/sensors 104, a signal processor 108, a console 110 and a display or monitor 112. The one or more field generator/sensors 104 may be magnetic field generators/sensors. The monitor 112 can be attached to the console 110 or can be mounted separately from the console 110.

As shown in FIG. 1, an operator 114, such as a physician, operates the medical system 100 to perform a medical procedure on a patient 116. The operator 114 uses the wireless medical tool 102 when performing a portion of the medical procedure. During other portions of the medical procedure, the wireless tool 102 is not used.

An operator 114 may insert the wireless medical tool 102 into a portion of patient anatomy, such as a nasal cavity or vascular system of the patient 116 so that a tip 56 of the wireless medical tool 102 enters a portion of interest of the patient anatomy. The control console 24 may use magnetic position sensing to determine position coordinates of the tip 56 in a three dimensional space inside the patient 116. To determine the position coordinates, a driver circuit 34 in the control console 24 may drive, via connector, 44 field generator 104 to generate magnetic fields within the anatomy of the patient 116.

In one embodiment, the field generator 104 may be a location pad. The field generator 104 may be located beneath the patient's head if the wireless tool is being used for an ENT procedure. Alternatively, the field generator 104 may be located beneath the patient's torso if the wireless medical tool is being used for a cardiac procedure.

The field generator 104 may include one or more emitter coils, placed at known positions external to the patient 116, which are configured to generate magnetic fields in a predefined working volume that contains a portion of interest of the patient anatomy. Each of the emitting coils is driven by a different frequency to emit a constant magnetic field in a three-dimensional space.

The medical system 100 uses the electromagnetic fields generated and detected by the field generator 104 to, among other things, calculate and determine the location of a wireless medical tool in a three dimensional space. Based on the amplitude and phase of the magnetic fields generated by the emitting coils, a magnetic field location sensor 38, in the tip 56 of the wireless medical tool 102, is configured to the determine the position of the receiving coil in a three dimensional space and generate electrical signals. The electrical signals associated with the position of the wireless medical tool 102 are wirelessly communicated to the control console 24 via a wireless communication device at the wireless medical tool 102. The wireless medical tool 102 may be equipped with a wireless input/output (I/O) interface 42 in the control console 24. The wireless I/O interface 42 may operate in accordance with any suitable wireless communication protocol or standard, such as for example, infrared (IR), radio frequency (RF), Bluetooth, one of the IEEE 802.11 family of standards (e.g., Wi-Fi), or the HiperLAN standard. The position sensors may include one or more wireless sensor nodes integrated on a substrate. The substrate may be flexible or it may be rigid. The one or more wireless sensor nodes may include a wireless transmit/receive unit (WTRU) enabling local digital signal processing, a radio link, and a miniaturized rechargeable battery, as described in more detail below.

The wireless I/O interface 42 may enable the control console 24 to interact with the wireless medical tool 102 and the position sensors. Based on the electrical impulses received from the surface electrodes 46 and the position sensors and the electrical signals received from the wireless medical tool 102 via the wireless I/O interface 42 and other components of medical system 100, the signal processor 108 may determine the location of the tool in a three dimensional space and generate the display information 52, which may be shown on a display 112.

The signal processor 108 is configured to process the signals to determine the position coordinates of the tip 56 in a three dimensional space, which include both location and orientation coordinates. The method of position sensing described hereinabove may be implemented in a mapping system similar to those produced by Biosense Webster Inc., of Diamond Bar, Calif., and is described in detail in the patents and the patent applications cited herein.

The magnetic field location sensor 38 transmits a signal to the control console 24 which indicates location coordinates of the tip 56 of the wireless medical tool 102 in three dimensional space. The magnetic field location sensor 38 may include one or more miniature receiver coils (not shown) and may include multiple miniature coils oriented along different axes. Alternatively, the magnetic field location sensor 38 may include another type of magnetic sensor or position transducers of other types, such as impedance-based or ultrasonic location sensors. Although FIG. 1 shows the wireless medical tool 102 having a single location sensor, embodiments may include tools with more than one location sensor.

The wireless medical tool 102 may also include a force sensor 54 contained within the tip 56. The force sensor 54 may measure a force applied by a tip 56 of the wireless medical tool 102 to the patient tissue and generating a signal that is sent to the control console 24. The force sensor 54 may include a magnetic field transmitter and a receiver connected by a spring in the tip 56, and may generate an indication of the force based on measuring a deflection of the spring. Further details of this type of tool and force sensor are described in U.S. Patent Application Publications 2009/0093806 and 2009/0138007 and are incorporated herein by reference. Alternatively, the tip 56 may include another type of force sensor that may use, for example, fiber optics or impedance measurements.

The wireless medical tool 22 may include an electrode 48 coupled to the tip 56 and configured to function as an impedance-based position transducer. Additionally or alternatively, the electrode 48 may be configured to measure a physiological property, for example impedance of a tissue. The electrode 48 may be configured to apply radio frequency (RF) energy to ablate tissue or for coagulation applications. The wireless medical tool 102 may also include an accelerometer 32 in the tip 56 to detect movement of the wireless medical tool 102.

Although the example medical system 100 may be configured to measure the position of the tip 56 using magnetic-based sensors, other position tracking techniques may be used (e.g., impedance-based sensors). Magnetic position tracking techniques are described, for example, in U.S. Pat. Nos. 5,391,199, 5,443,489, 6,788,967, 6,690,963, 5,558,091, 6,172,499, and 6,177,792 and are incorporated herein by reference. Impedance-based position tracking techniques are described, for example, in U.S. Pat. Nos. 5,983,126, 6,456,828 and 5,944,022 and are incorporated herein by reference.

The signal processor 108 may be included in a general-purpose computer, with a suitable front end and interface circuits for receiving signals from the wireless medical tool 102 and may be configured to control the other components of the control console 24. The signal processor 108 may be programmed, using software, to carry out the functions that are described herein. The software may be downloaded to the control console 24 in electronic form, over a network, for example, or it may be provided on non-transitory tangible media, such as optical, magnetic or electronic memory media. Alternatively, some or all of the functions of the signal processor 108 may be performed by dedicated or programmable digital hardware components.

Additionally or alternatively, the wireless medical tool 102 and the position sensors may communicate with the control console 24 and one another via a wireless interface. For example, U.S. Pat. No. 6,266,551 describes, inter alia, a wireless tool that is not physically connected to a signal processing and/or computing apparatus and is incorporated herein by reference. Rather, a transmitter/receiver is attached to the proximal end of the tool. The transmitter/receiver communicates with a signal processing and/or computer apparatus using wireless communication methods, such as infrared (IR), radio frequency (RF), wireless, Bluetooth, or acoustic transmissions.

During diagnostic treatment, the signal processor 108 may present the display information 52 and may store data representing the information 52 in a memory 58. The memory 58 may include any suitable volatile and/or non-volatile memory, such as random access memory or a hard disk drive. The operator 114 may be able to manipulate the display information 52 using one or more input devices 59. Alternatively, the medical system 100 may include a second operator that manipulates the control console 24 while the operator 114 manipulates the wireless medical tool 102. It should be noted that the configuration shown in FIG. 1 is exemplary. Any suitable configuration of the medical system 100 may be used and implemented.

When the wireless medical tool 102 is not in use, the system 100 may detect that the wireless medical tool 102 is "out of range," e.g., the wireless medical tool 102 is in a location that is not in accordance with use of the tool, and switch the tool to a hibernation mode. The system 100 calculates a location based on a signal amplitude from the wireless medical tool 102, and whether a certain motion and/or time threshold is exceeded. If the motion and/or time threshold is exceeded, the system 100 may determine that the wireless medical tool 102 is in position to be used. If the wireless medical tool 102 had been in hibernation mode, and it now exceeds the motion and/or time threshold, the power to the location sensor may be switched on or activated. Throughout the medical procedure, when the motion and/or time threshold are exceeded, the wireless medical tool 102 remains active or in use. Otherwise, when the motion and/or time threshold are less than a predetermined threshold, the wireless medical tool 102 is placed and maintained in hibernation mode.

Figure 2:
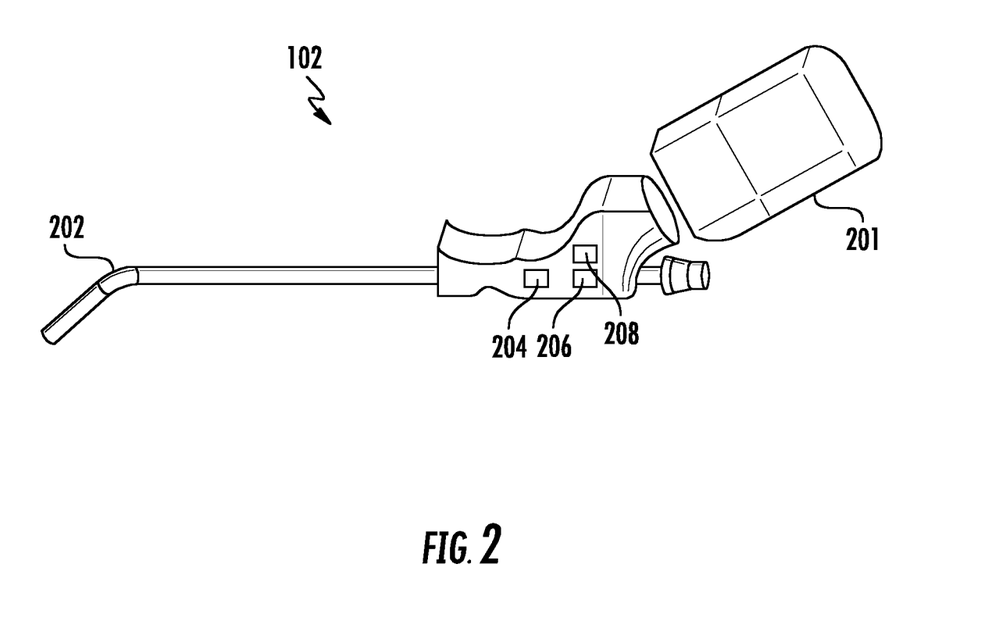
FIG. 2 is a diagram of an example wireless medical tool.

FIG. 2 shows an exemplary wireless medical tool 102. The wireless medical tool 102 may obtain power by one or more batteries via a battery pack or battery holder 201. The battery pack or battery holder 201 may be fixed or may be removable as shown in FIG. 2. Current wireless medical tools provide short-range radio technology to enable wireless communications. These technologies enable the wireless transmission and receiving of signals; however, they require significant power consumption by the medical tool. The present system aims to conserve and manage power by limiting power consumption from wireless communications by switching to a low power mode during non-use of the wireless medical tool 102. The low power mode enables reduction of battery consumption to preserve and extend the duration of usage of the tool.

The wireless medical tool 102 may comprise a detection mechanism comprising an accelerometer 202, an inductor 204, and resistors 206, 208 for transmitting signals, e.g., voltage, to the signal processor 108. In this example, the accelerometer 202 is shown near the tip of the wireless medical tool 102, which may be preferable if the wireless medical tool 102 is flexible. If the wireless medical tool is rigid, the accelerometer 202 may be located in the handle. Locating the accelerometer 202 in the handle may help reduce interference of the magnetic field received by the inductor 204 in the tip. The inductor 204 may also be referred to as a location sensor, magnetic sensor, or magnetic location sensor. The inductor 204 may be passive, and may not consume power. As the wireless medical tool 102 is moved to a location where it will be used, e.g., inductor 204 matches the specific frequency of the location, the voltage on resistor 208 increases and exceeds a frequency threshold, which causes the wireless medical tool 102 to be enabled or activated. Otherwise, while the voltage remains low, the wireless medical tool 102 remains in hibernation mode. When the wireless medical tool 102 is enabled, the signal processor 108 communicates with the wireless medical tool 102 wirelessly using a suitable wireless communication method such as WiFi, Bluetooth, IR, etc. The signal processor 108 receives this wireless communication from the wireless medical tool 102 and calculates the location and orientation of the wireless medical tool 102 in a three-dimensional space.

Low power mode may include not transmitting or receiving wireless communications between the wireless medical tool 102 and the signal processor 108, as well as an overall reduced power during periods of non-use of the wireless medical tool 102. Other reduced power management schemes may be employed. In low power mode, wireless communication can be limited to detection only.

Furthermore, the wireless medical tool 102 may generate either a visible or audible indication to indicate sufficient battery power is available. A visible indication may include an illuminating light emitting diode (LED) and/or an indicator on the monitor 112, while an audible indication may include a periodically sounding audible tone. The audible indication may be produced through speakers (not shown) in the console 110. A visible or audible indication may also be used to indicate when the battery power falls below a certain threshold.

Figure 3:
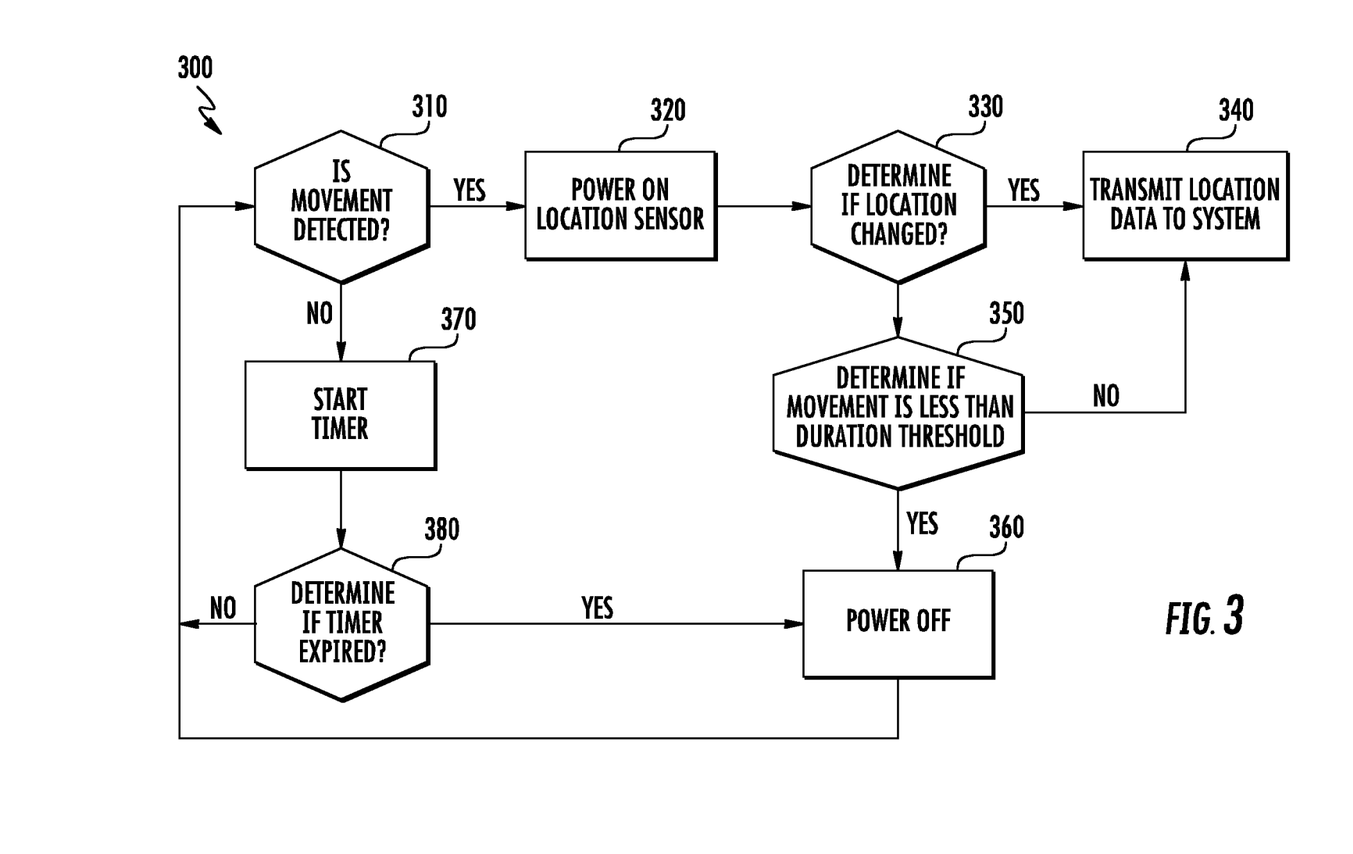
FIG. 3 is a flow diagram of a method for activating a power mode and/or a hibernation mode of a wireless medical tool in accordance with an embodiment of the present invention.

FIG. 3 is a flow diagram of an example power saving method 300 for use in a wireless medical tool. The wireless tool may include an accelerometer to detect motion as described above. In this example, the wireless medical tool may initially be in a power saving mode. If the wireless medical tool detects motion at 310, the wireless medical tool may power on the location sensor 320. The location sensor may then scan for magnetic frequencies to determine if the tool is within the magnetic operating field, and whether the user location of the wireless medical tool has changed 330. If the location of the wireless medical tool has changed, the wireless medical tool may transmit data to the system 340. If the location has not changed at 330, or if the wireless medical tool is outside the magnetic operating field, the wireless medical tool may determine whether the detected movement is below a duration threshold 350. If the detected movement is for a duration that is greater than a duration threshold, the wireless medical tool may continue to transmit data to the system 340. If the detected movement is less than a duration threshold, the wireless medical tool may shut off power to the location sensor 360 and enter a low power or hibernation mode. The duration threshold may range from one to five minutes. For example, the duration threshold may be set to three minutes, and may be configurable by the user.

If motion is not detected at 310, the wireless medical tool may start a timer 370. If the timer expires before the next motion is detected 380, the wireless medical tool may shut off power to the location sensor 360 and enter a low power or hibernation mode. A summary of the correlation between the location sensor and the accelerometer is shown below in Table 1.

TABLE 1

| Change in Accelerometer | Change in Location Sensor | Power Off |
| --- | --- | --- |
| No | No | Yes |
| Yes | No | Yes |
| No | Yes | No |
| Yes | Yes | No |

Figure 4:
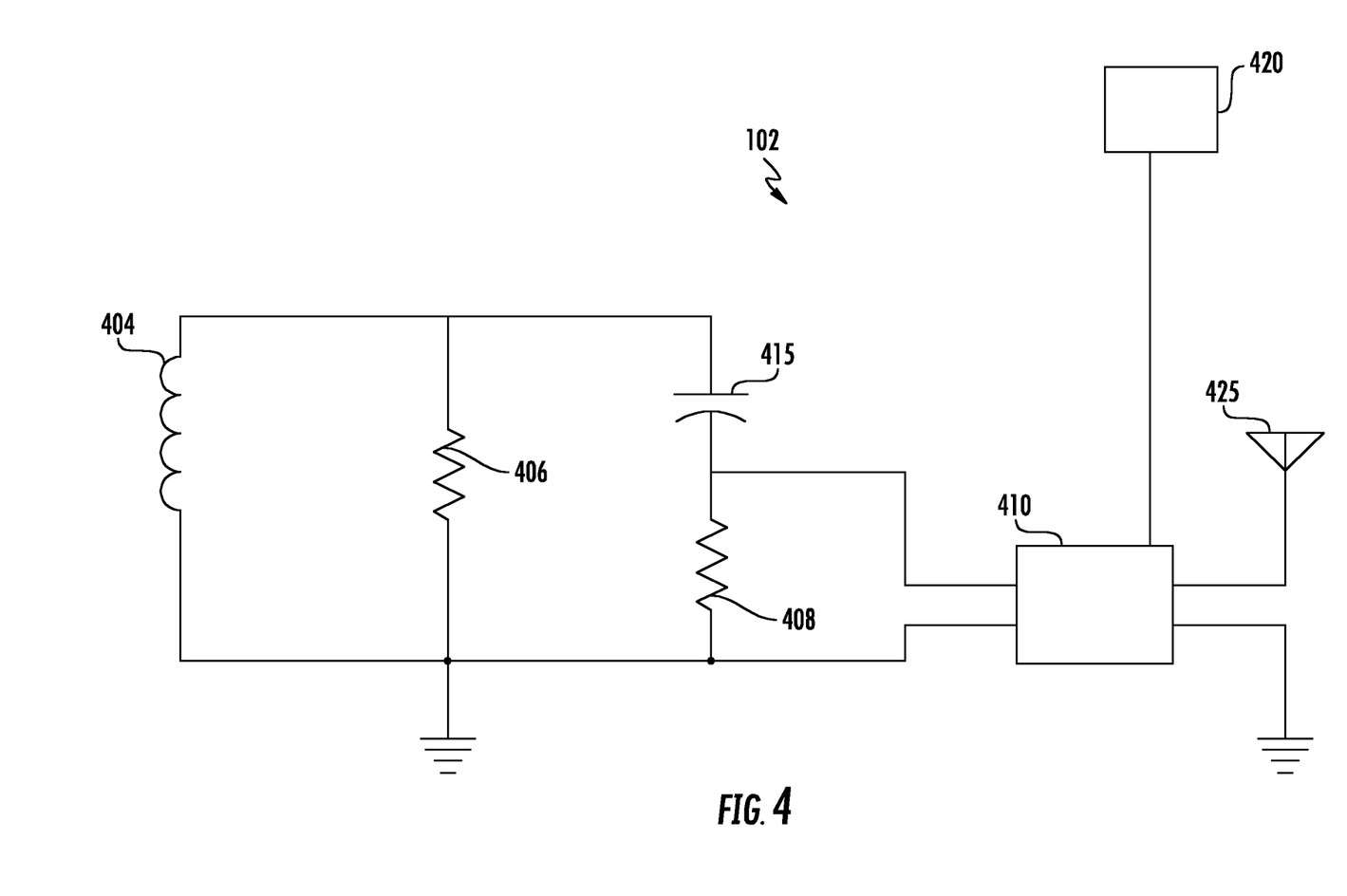
FIG. 4 is an electrical diagram of another example wireless medical tool.

FIG. 4 is an electrical diagram of an example embodiment of the power management system. The wireless medical tool 102 may include an inductor 404, resistors 406, 408, processor 410, capacitor 415, an accelerometer 420, and a transmitter 425. The transmitter 425 may transmit location data to a system console. The transmitter 425 may also be configured as a transceiver such that it is capable of receiving data from the system console in addition to transmitting data. In this example, a processor 410 may receive a signal from the inductor 404 indicating a change in location. The processor 410 may also receive a signal from the accelerometer 420 indicating motion. The processor 410 may be configured to correlate the information received from the inductor 404 and accelerometer 420 to determine whether to enter into a power saving mode. For example, if the accelerometer 420 readings are high and the inductor 404 readings are high, then the processor 410 may determine that the wireless medical tool 102 is in use and maintain power to the inductor 404.

In an example where the accelerometer 420 readings are low and the inductor 404 readings are high, then the processor 410 may determine that they physician has placed the wireless medical tool 102 near the magnetic field generator and is not using the wireless medical tool 102. In this example, the processor 410 may shut off power to the inductor 404 and enter a low power or hibernation mode.

In an example where the accelerometer 420 readings are high and the inductor 404 readings are low, the processor 410 may determine that the wireless medical tool 102 is not in use or is being cleaned. In this example, the processor 410 may shut off power to the inductor 404 and enter a low power or hibernation mode.

The determination of high and low accelerometer readings and inductor readings may be based on an amplification level of a circuit. A high and low threshold may be user configurable for both the accelerometer reading and the inductor reading.

It should be understood that many variations are possible based on the disclosure herein. Although features and elements are described above in particular combinations, each feature or element can be used alone without the other features and elements or in various combinations with or without other features and elements.

The methods provided include implementation in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which implements automatic temperature control based on occupant clothing.

The methods or flow charts provided herein can be implemented in a computer program, software, or firmware incorporated in a non-transitory computer-readable storage medium for execution by a general purpose computer or a processor. Examples of non-transitory computer-readable storage mediums include a ROM, a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A wireless surgical tool comprising:
   a detector configured to detect motion of the wireless surgical tool in a three dimensional (3D) space and provide motion information indicating whether or not the wireless surgical tool moves;
   a sensor configured to provide, using a signal received from a magnetic field generator when the sensor is within a magnetic operating field of the 3D space, location information indicating a location of the wireless surgical tool in the magnetic operating field of the 3D space;
   a timer configured to measure a predetermined time period upon the detector providing motion information indicating that the wireless surgical tool has not moved;
   a transmitter configured to transmit the location information to a system console; and
   a processor configured to:
      maintain power of the wireless surgical tool in
         a first power mode wherein the processor maintains power to the detector and the sensor and the timer and the transmitter, and
         a second power mode wherein the processor maintains power to the detector and the timer and the transmitter without power to the sensor;
      upon determining via the detector that the wireless surgical tool has not moved,
         start the timer;
         power off the sensor and maintain power of the wireless surgical tool in the second power mode when the wireless surgical tool has not moved during the predetermined period;
      upon determining via the detector that the wireless surgical tool has moved,
         power on the sensor and maintain power of the wireless surgical tool in the first power mode,
         determine, via the sensor, the location information further comprising whether or not:
            the location of the wireless surgical tool changes; and
            the wireless surgical tool is within the magnetic operating field;
         correlate the motion information and the location information;
         power off the sensor based on a correlated information and maintain power of the wireless surgical tool in the second power mode; and
         transmit the correlated information to the system console.

2. The wireless surgical tool of claim 1, wherein the detector is an accelerometer.

3. The wireless surgical tool of claim 1, wherein the sensor is an inductor.

4. The wireless surgical tool of claim 3, wherein the inductor is a magnetic inductor.

5. The wireless surgical tool of claim 1, wherein on a condition that at least one of the location of the wireless surgical tool does not change and the wireless surgical tool is not within the magnetic operating field, the processor is further configured to determine whether the motion information is less than a duration threshold.

6. The wireless surgical tool of claim 1, wherein the processor is further configured to power off the sensor on a condition that the motion information indicates movements less than a duration threshold and on a condition that the location of the wireless surgical tool has not changed.

7. A method for use in a wireless surgical tool, the method comprising:
   providing a detector configured to detect motion of the wireless surgical tool in a three dimensional (3D) space and provide motion information indicating whether or not the wireless surgical tool moves;
   providing a location sensor configured to provide location information indicating whether or not the location of the wireless tool changes and whether the wireless surgical tool is within a magnetic operating field of the 3D space;
   providing a timer configured to measure a predetermined time period upon the detector providing motion information indicating that the wireless surgical tool has not moved;
   providing a processor configured to maintain power of the wireless surgical tool in
      a first power mode wherein the processor maintains power to the detector and the sensor and the timer, and
      a second power mode wherein the processor maintains power to the detector and the timer without power to the sensor;
   determining via the detector that the wireless surgical tool has not moved;
   starting the timer;
   determining that the wireless surgical tool has not moved during the predetermined time period;
   powering off the sensor and maintaining power of the wireless surgical tool in the second power mode;
   determining via the detector that the wireless surgical tool has moved;
   powering on the sensor and maintaining power of the wireless surgical tool in the first power mode;
   enabling the location sensor to generate the location information indicating a location of the wireless surgical tool in the magnetic operating field of the 3D space;
   determining, via the location sensor, the location information further comprising whether or not the location of the wireless surgical tool changes and whether or not the wireless surgical tool is within the magnetic operating field;
   correlating the motion information and the location information;
   powering off the location sensor based on a correlated information and maintaining power of the wireless surgical tool in the second power mode; and
   transmitting the location information to a control console.

8. The method of claim 7 further comprising:
   continuing to determine whether or not movement is detected on a condition that the timer has not expired.

9. A medical system comprising:
   a wireless surgical tool;
   a field generator;
   a console; and
   a display;
   wherein the wireless surgical tool comprises:
      a detector configured to detect motion of the wireless surgical tool in a three dimensional (3D) space and provide motion information indicating whether or not the wireless surgical tool moves;
      a sensor configured to provide, using a signal received from the magnetic field generator when the sensor is within a magnetic operating field of the 3D space, location information indicating a location of the wireless surgical tool in the magnetic operating field of the 3D space;

a timer configured to measure a predetermined time period upon the detector providing motion information indicating that the wireless surgical tool has not moved;

a transmitter configured to transmit the location information to the console wherein the console is configured to process the location information and display the location information on the display; and a processor configured to:
receive the motion information from the detector and the location information from the sensor;
maintain power of the wireless surgical tool in
a first power mode wherein the processor maintains power to the detector and the sensor and the timer and the transmitter, and
a second power mode wherein the processor maintains power to the detector and the timer and the transmitter without power to the sensor;
upon determining via the detector that the wireless surgical tool has not moved,
start the timer;
power off the sensor and maintain power of the wireless
surgical tool in the second power mode when the wireless surgical tool has not moved during the predetermined period;
upon determining via the detector that the wireless surgical tool has moved,
power on the sensor and maintain power of the wireless surgical tool in the first power mode,
determine, via the sensor, the location information further comprising whether or not the location of the wireless surgical tool changes and whether or not the wireless surgical tool is within the magnetic operating field;
correlate the motion information and the location information;
power off the sensor based on a correlated information and maintain power of the wireless surgical tool in the second power mode; and
transmit the correlated information to the console.

10. The medical system of claim 9, wherein the detector is an accelerometer.

11. The medical system of claim 9, wherein the sensor is an inductor.

12. The medical system of claim 11, wherein the inductor is a magnetic inductor.

13. The medical system of claim 9, wherein on a condition that at least one of the location of the wireless surgical tool does not change and the wireless surgical tool is not within the magnetic operating field, the processor is further configured to determine whether or not the motion information is less than a duration threshold.

14. The medical system of claim 9, wherein the processor is further configured to power off the sensor on a condition that the motion information indicates movement less than a duration threshold and on a condition that the location of the wireless surgical tool does not change.

* * * * *

UNITED STATES PATENT AND TRADEMARK OFFICE
CERTIFICATE OF CORRECTION

| | | |
|---|---|---|
| PATENT NO. | : 11,497,560 B2 | Page 1 of 1 |
| APPLICATION NO. | : 15/581230 | |
| DATED | : November 15, 2022 | |
| INVENTOR(S) | : Vadim Gliner et al. | |

It is certified that error appears in the above-identified patent and that said Letters Patent is hereby corrected as shown below:

In the Specification
In Column 1, Lines 32-33, delete "transmission of the location information of the location information may" and insert -- transmission of the location information may --, therefor.
In Column 2, Lines 21-23, delete "transmission of the location information of the location information may" and insert -- transmission of the location information may --, therefor.
In Column 2, Line 54, delete "IrDA (infrared data)," and insert -- IrDA (Infrared Data Association), --, therefor.
In Column 3, Line 43, delete "wireless medical tool 38," and insert -- wireless medical tool 102, --, therefor.
In Column 3, Line 54, delete "wireless tool 102" and insert -- wireless medical tool 102 --, therefor.
In Column 3, Lines 63-64, delete "connector, 44 field generator 104" and insert -- connector, field generator 104 --, therefor.
In Column 4, Lines 19-20, delete "configured to the determine" and insert -- configured to determine --, therefor.
In Column 4, Lines 29-30, delete "infra-red (IR)," and insert -- infrared (IR), --, therefor.
In Column 4, Line 43, delete "electrodes 46" and insert -- electrodes 48 --, therefor.
In Column 5, Line 18, delete "wireless medical tool 22" and insert -- wireless medical tool 102 --, therefor.
In Column 8, Line 17, delete "that they physician" and insert -- that the physician --, therefor.

In the Claims
In Column 9, Line 20, in Claim 1, delete "tool in" and insert -- tool in: --, therefor.
In Column 10, Line 17, in Claim 7, delete "tool in" and insert -- tool in: --, therefor.
In Column 11, Line 12, in Claim 9, delete "tool in" and insert -- tool in: --, therefor.
In Column 11, Lines 24-26, in Claim 9, delete "surgical tool . . . . period;" and insert the same at Line 23, after "wireless" as a continuation sub-point.

Signed and Sealed this
Twelfth Day of September, 2023

Katherine Kelly Vidal
*Director of the United States Patent and Trademark Office*